(12) United States Patent
Boussignac et al.

(10) Patent No.: US 10,806,888 B2
(45) Date of Patent: Oct. 20, 2020

(54) RESPIRATORY ASSISTANCE DEVICE, NASAL APPARATUS AND RESPIRATORY ASSISTANCE MASK

(71) Applicants: VYGON, Ecouen (FR); Georges Boussignac, Antony (FR)

(72) Inventors: Georges Boussignac, Antony (FR); Jean-Luc Carrez, Ecouen (FR); Elodie Bertheuil, Auvers sur Oise (FR); Laurent Lesimple Bobert, Tremblay en France (FR); Cyril Riga, Agnetz (FR)

(73) Assignees: VYGON, Ecouen (FR); Georges Boussignac, Antony (FR)

( * ) Notice: Subject to any disclaimer, the term of this patent is extended or adjusted under 35 U.S.C. 154(b) by 981 days.

(21) Appl. No.: 15/318,510

(22) PCT Filed: Jun. 11, 2015

(86) PCT No.: PCT/FR2015/051553
§ 371 (c)(1),
(2) Date: Dec. 13, 2016

(87) PCT Pub. No.: WO2015/189525
PCT Pub. Date: Dec. 17, 2015

(65) Prior Publication Data
US 2017/0119990 A1    May 4, 2017

(30) Foreign Application Priority Data

Jun. 13, 2014   (FR) .................................. 14 55395

(51) Int. Cl.
*A61M 16/08*    (2006.01)
*A61M 16/16*    (2006.01)
(Continued)

(52) U.S. Cl.
CPC .... *A61M 16/0875* (2013.01); *A61M 16/0012* (2014.02); *A61M 16/0666* (2013.01);
(Continued)

(58) Field of Classification Search
CPC .............. A61M 16/00; A61M 16/0012; A61M 16/0096; A61M 16/04; A61M 16/042;
(Continued)

(56) References Cited

U.S. PATENT DOCUMENTS

| 5,036,847 A | * | 8/1991 | Boussignac | ........... A61M 16/12 128/203.12 |
| 5,538,002 A | | 7/1996 | Boussignac et al. | |

(Continued)

FOREIGN PATENT DOCUMENTS

| EP | 0 701 834 A1 | 3/1996 |
| EP | 0 978 291 A1 | 2/2000 |

(Continued)

OTHER PUBLICATIONS

International Search Report, dated Sep. 8, 2015, from corresponding PCT application.

*Primary Examiner* — Joseph D. Boecker
(74) *Attorney, Agent, or Firm* — Nixon & Vanderhye

(57) ABSTRACT

A respiratory assistance device (1) for a patient, includes a tubular element forming a main channel (5) (207) which is to be connected via the distal end (7) thereof to an airway of the patient, the main channel connecting to the exterior of the respiratory system of the patient via the proximal end (6) thereof, the device further including at least one auxiliary channel (8) (209) allowing the injection of jets of breathable gas for ventilation of the patient via the distal outlet openings (17) of the auxiliary channel(s), the outlet openings opening out into the main channel in the vicinity of the distal end thereof, deflection elements (14b) (14a) allowing the deflection of gas jets to the interior of the main channel, and an internal jet separator, coaxial and central to the main channel, which further ensures diversion of the flow for expired gases.

14 Claims, 4 Drawing Sheets

(51) Int. Cl.
*A61M 16/00* (2006.01)
*A61M 16/12* (2006.01)
*A61M 16/06* (2006.01)
*A61M 16/04* (2006.01)

(52) U.S. Cl.
CPC .......... *A61M 16/127* (2014.02); *A61M 16/16* (2013.01); *A61M 16/04* (2013.01); *A61M 2016/0021* (2013.01); *A61M 2016/0027* (2013.01); *A61M 2202/0208* (2013.01); *A61M 2205/583* (2013.01); *A61M 2206/14* (2013.01)

(58) Field of Classification Search
CPC .............. A61M 16/06; A61M 16/0666; A61M 16/0672; A61M 16/0816; A61M 16/085; A61M 16/0858; A61M 16/0875; A61M 16/125; A61M 16/127; A61M 16/16; A61M 2016/0027; A61M 15/08; A62B 23/06; A61F 5/08
See application file for complete search history.

(56) References Cited

U.S. PATENT DOCUMENTS

| | | | |
|---|---|---|---|
| 6,273,087 B1* | 8/2001 | Boussignac | A61M 16/12 128/200.12 |
| 6,363,935 B1 | 4/2002 | Boussignac | |
| 2001/0042548 A1 | 11/2001 | Boussignac | |
| 2003/0159696 A1 | 8/2003 | Boussignac et al. | |
| 2004/0050389 A1* | 3/2004 | Boussignac | A61M 16/12 128/207.14 |
| 2009/0044807 A1 | 2/2009 | Boussignac | |
| 2010/0229862 A1* | 9/2010 | Boussignac | A61M 16/127 128/204.18 |
| 2010/0229865 A1* | 9/2010 | Boussignac | A61M 16/12 128/205.24 |
| 2010/0282262 A1 | 11/2010 | Boussignac | |
| 2012/0255551 A1* | 10/2012 | Boussignac | A61M 16/127 128/204.18 |
| 2014/0053841 A1 | 2/2014 | Ratner | |

FOREIGN PATENT DOCUMENTS

| | | |
|---|---|---|
| EP | 2 228 088 A1 | 9/2010 |
| FR | 894 280 A | 4/1943 |
| FR | 0 390 684 A1 | 10/1990 |
| FR | 2 782 925 A1 | 3/2000 |
| FR | 2 813 197 A1 | 3/2002 |
| FR | 2 827 778 A1 | 1/2003 |
| FR | 2 836 384 A1 | 8/2003 |
| FR | 2 911 073 A1 | 7/2008 |
| FR | 2 921 840 A1 | 4/2009 |
| FR | 2 942 967 A1 | 9/2010 |
| FR | 2 973 708 A1 | 10/2012 |
| WO | 2003039638 A1 | 5/2003 |
| WO | 2007118973 A1 | 10/2007 |
| WO | 2008/113913 A | 9/2008 |
| WO | 2014/033401 A1 | 3/2014 |

\* cited by examiner

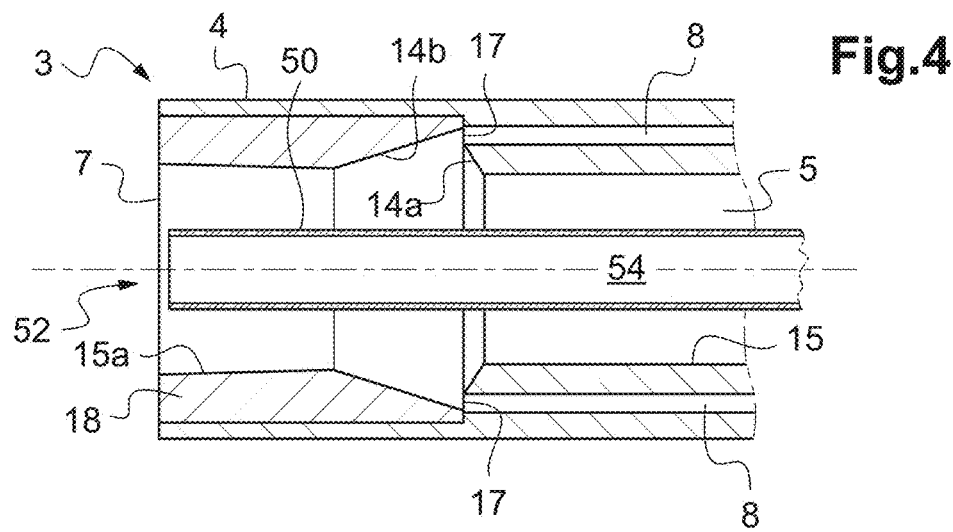
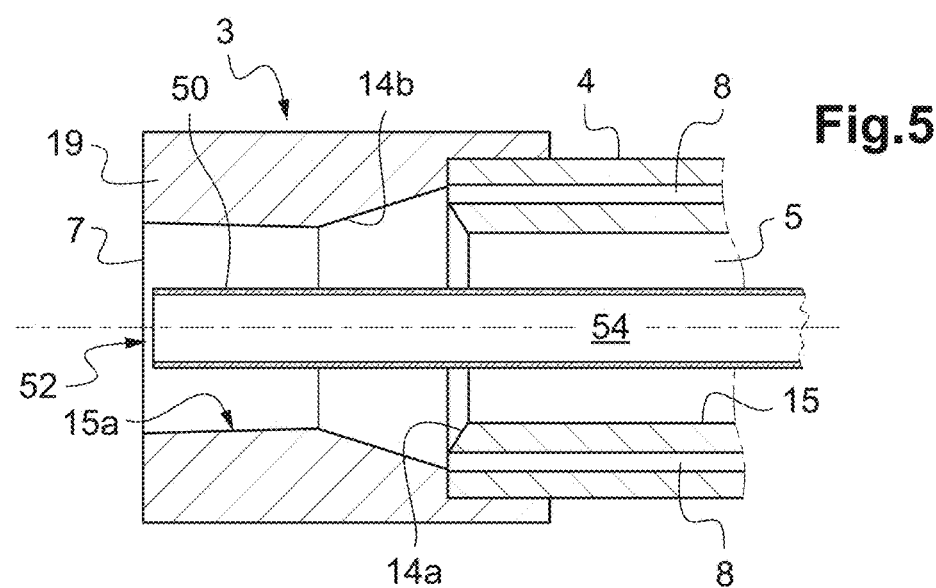
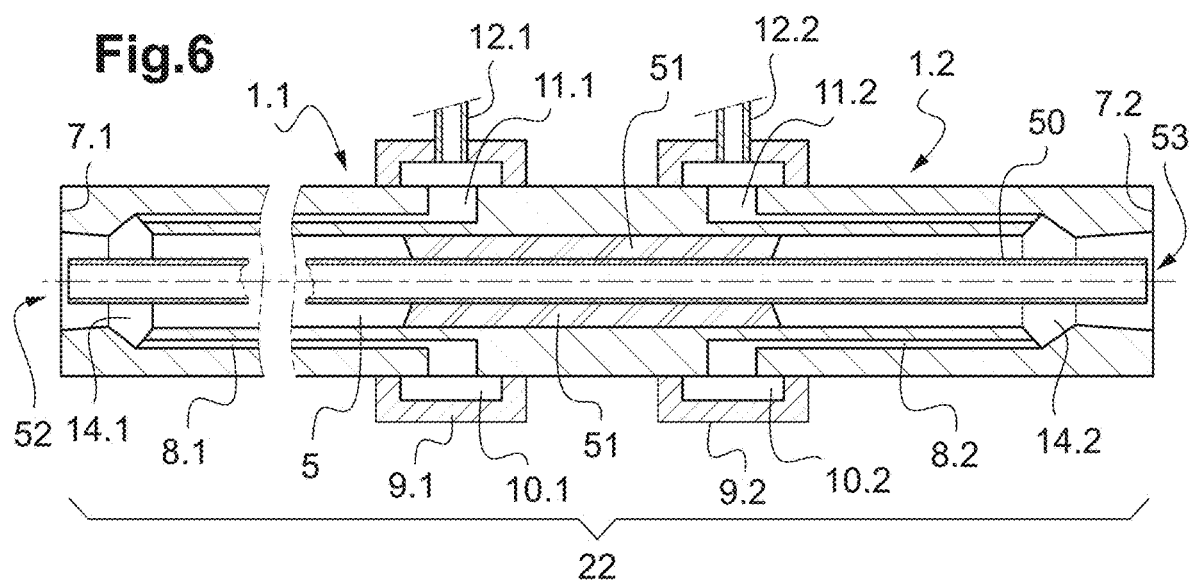

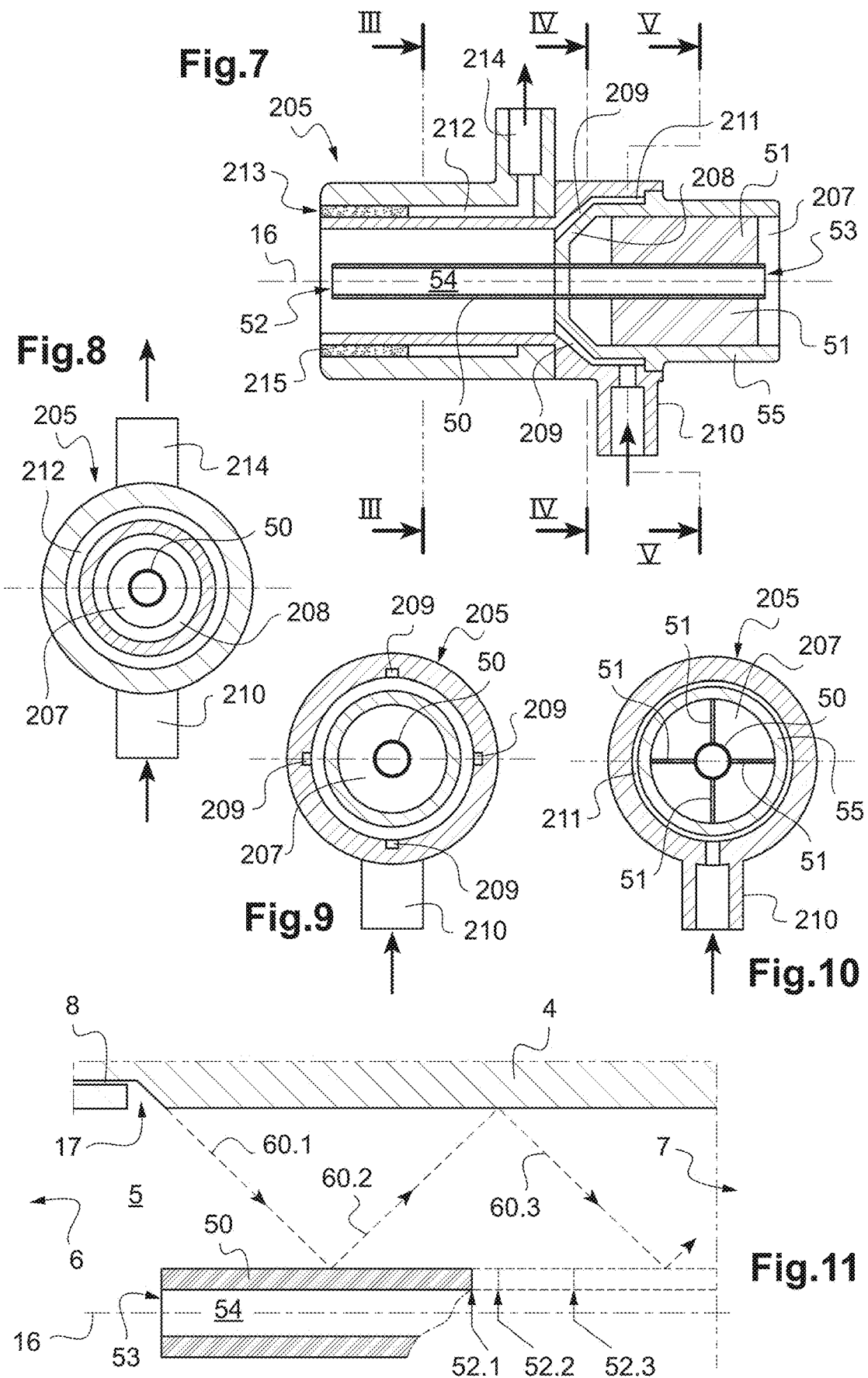

US 10,806,888 B2

RESPIRATORY ASSISTANCE DEVICE, NASAL APPARATUS AND RESPIRATORY ASSISTANCE MASK

BACKGROUND OF THE INVENTION

Field of the Invention

The present invention has for object an advanced respiratory assistance device, usable on patients whose spontaneous breath is absent or insufficient, whether they are placed or not under artificial respiration. It is more particularly adapted to the respiratory assistance devices invented by Mr. Georges Boussignac.

Description of the Related Art

The principle underlying the respiratory assistance device invented by Mr. Boussignac consists in injecting, through a set of auxiliary channels, at least one pressurized breathable gas into the lumen of a tubing connected to the patient airways. This assistance device has the particularity to be of the open type, i.e. the tubing may remain open to free air, hence allowing the passage of probes or other accessories for the patient monitoring or treatment. More precisely, the assistance device is formed of a tubular element or tube that forms a main channel and that is intended to be connected by its distal end to an airway of a patient so that said main channel connects the respiratory system of said patient to the outside. The device further includes at least one auxiliary channel allowing the injection of a jet of breathable gas intended for the ventilation of said patient and emerging through a distal outlet orifice into said main channel in the vicinity of the distal end of the latter. In this assistance device, opposite the distal outlet orifice of each auxiliary channel, are provided means for deflecting said breathable gas jets towards the inside of said main channel.

Hence, the jet of pressurized breathable gas passing through said auxiliary channel is deflected towards the central axis of the main channel, when it enters the latter. Generally, several jets are created and deflected towards each other towards the central axis of the main channel. The jets hence meet each other towards the centre of the main channel, creating therein a zone of turbulences and pressure. Downstream said deflection means, i.e. inside the main channel, the pressure of said jet of breathable gas falls and the jet goes out with a low pressure through the distal end of the tubular element. Experience has shown that, downstream the distal outlet orifice of the tubular element, the pressure is low and maintained constant in the whole respiratory space. Moreover, this pressure depends on the flow rate of breathable gas in the auxiliary channels and we have hence also a simple means for adjusting the pressure by acting on the gas flow rate in the auxiliary channels.

This respiratory assistance device may hence allow holding a continuous positive pressure in the respiratory system of the patient and avoids a sagging of the pulmonary alveoli walls prejudicial to the ventilation. Such an application of this device is called CPAP for "continuous positive airway pressure".

This respiratory assistance device has also appeared very useful within the framework of the cardiac, and more generally cardiopulmonary, resuscitation, by manual or mechanical external thoracic massage.

This assistance device, the knowledge of which can be completed from the patent application FR89/04280, has been subjected to various improvements in the following patent applications given by way of non-exhaustive example: EP0390684, WO2008113913, EP2228088, FR2942967, WO2007118973, FR2911073, FR2813197, WO2003039638, FR2827778, EP0978291, FR2921840, FR2782925, FR2836384 and EP0701834.

Moreover, it will be seen that these various improvements may be implemented within the framework of the present invention. In particular, the nebulization of liquid products, the resuscitation assistance, the nasal use, the dual-flow . . . .

This device has provided a certain comfort to the patients and to the nursing staff due to the fact that it is of the open type. Moreover, it is of relatively simple principle and manufacture.

However, the device, as it has been proposed, has for drawback to cause a nebulization or atomization of the patient's expectorations or haemoptyses when these latter pass through the zone of turbulences in which the deflected jets meet each other in the main channel of the device of Mr. Boussignac. It hence exists an important risk of contamination of the staff if the patient is affected with a contagious infection. In particular, during the cardiopulmonary resuscitation by manual or mechanical external thoracic massage, haemoptyses may occur. Moreover, it may occur regurgitations, which are also liable to be nebulized or atomized.

A simple solution would be to add a filter at the proximal outlet of the respiratory assistance device. However, this implies to regularly check the tightness thereof to gas, which is not always easy and simple in emergency resuscitation conditions.

It is proposed to make a by-pass in the zone of the deflected jets, inside the main channel, thanks to a hollow by-pass inner tube.

Other solutions have been proposed in the state of the art, disclosed in the documents FR 2 973 708, US 2014/053841 and FR 2 813 197, but they implement no coaxial by-passes for the gases breathed out and/or breathed in and limited in extent to the zone of the deflected jets.

BRIEF SUMMARY OF THE INVENTION

The invention hence relates to a respiratory assistance device for a patient including a tubular element forming a main channel that is intended to be connected by its distal end to an airway of the patient, said main channel connecting the respiratory system of said patient to the outside by its proximal end, said device further including at least one auxiliary channel allowing the injection through one/several distal outlet orifice(s) of the auxiliary channel(s) of jet(s) of breathable gas(es) intended for the ventilation of said patient, said outlet orifice(s) emerging into said main channel in the vicinity of the distal end of the latter, deflection means allowing the deflection of the jets of breathable gas(es) towards the inside of said main channel and towards the distal end according to a determined inclination.

According to the invention, the device further includes a coaxial inner tube centred in the main channel, said inner tube of determined length having a distal end turned towards the distal end of the tubular element and a proximal end turned towards the proximal end of the tubular element, said determined length being such that said inner tube is extended at the maximum between the two distal and proximal ends of said respiratory assistance device, said inner tube intersecting/crossing the axis(es) of the deflected jets in order to form a jet breaker towards the centre of the main channel in a zone of meeting of said deflected jet axes and of said inner tube, and the inner tube is hollow and open at the two ends thereof in order to form a by-pass for the gases circulating in said device and in particular for the gases breathed out by the patient.

With respect to the known devices that may include an inner tubing for the suction of tracheo-pulmonary or gastric mucosities and that are probes of great length, the inner tube of the invention is of reduced length, essentially limited to the zone of the deflected jets of gas and it is not intended to pick up mucosities in situ during suctions or a stomach content or to perform measurements. The inner tube is fixed and is comprised in the respiratory assistance device, essentially limited in length in the zone of the jets of breathable gas(es) at the exit of the outlet orifices of the auxiliary channels, even if it can extend a little beyond, in particular for easiness of holding/fastening. The inner tube of the invention is hence a jet-breaking and by-passing tube.

In various embodiments of the invention, the following means, which can be used alone or in any technically possible combination, are used:

- the respiratory assistance device is integrated or added on at least one link element, the link element being in particular a facial mask or a nasal adapter, a laryngeal mask, a tubing for distal link to the patient airway, a tubing for the distal link of the inflatable cuff(s) sealing type, a tubing for the proximal link to a ventilation apparatus,
- the respiratory assistance device is intended to be implemented outside the patient, in particular integrated or added to a facial mask or a nasal adapter or a tubing for distal link to the patient airway,
- the respiratory assistance device is intended to be implemented inside the patient, in particular integrated or added to a laryngeal mask or to a tubing for the distal link to the patient airway or to a tubing for the distal link of the inflatable cuff(s) sealing type, including endotracheal,
- the main channel is cylindrical,
- the auxiliary channel(s) are made in the thickness of the wall of the tubular element,
- the device includes a set of auxiliary channels, said auxiliary channels being substantially parallel to the central axis of said tubular element over at least one part of their travels,
- the distal outlet orifice(s) of the auxiliary channel(s) emerge at the internal surface of the tubular element,
- the tubular element includes within its wall, in addition to the auxiliary channels allowing the injection of jet(s) of breathable gas(es), at least one annex auxiliary channel allowing the injection into the main channel through an annex distal outlet orifice of the annex auxiliary channel of products distinct from the breathable gas(es), in particular liquid(s),
- the tubular element includes within its wall, in addition to the auxiliary channels allowing the injection of jet(s) of breathable gas(s) and in addition to the potential annex auxiliary channel(s), at least one feeding duct allowing the passage of fluids, in particular gases or liquids, towards the patient,
- the tubular element includes within its wall, in addition to the auxiliary channel(s) allowing the injection of jet(s) of breathable gas(s) and in addition to the potential annex auxiliary channel(s), at least one measurement duct allowing the collection of fluid samples from the patient, in particular breathed-out gases or secretions, towards an external sampling and/or suction and/or measurement apparatus,
- the tubular element includes within its wall, in addition to the auxiliary channel(s) allowing the injection of jet(s) of breathable gas(s) and in addition to the potential annex auxiliary channel(s), at least one measurement duct allowing the measurement of the pressure of the respiratory gases on the distal side of the device,
- the inner tube is cylindrical,
- the external surface of the inner tube is substantially smooth,
- the external surface of the inner tube includes relief and recessed elements, in particular in the zone in which the deflected jet axes meet said inner tube,
- the inner tube is held in coaxial position inside the main channel by fins extending radially between the external surface of the inner tube and the internal surface of the tubular element, said fins being absent in the zone of the deflected jets,
- the fins are of reduced thickness,
- a tubular body is added inside the tubular element,
- preferably, the tubular body is added on the proximal side of the tubular element,
- a tubular body is added on the distal side of the tubular element,
- the inner tube is held in coaxial position inside the main channel by a single set of fins extending radially between the external surface of the inner tube and the internal surface of the tubular element or a proximal added tubular body, said set of fins being on the side of the proximal end of the tubular element, said fins being absent in the zone of the deflected jets,
- the inner tube is held in coaxial position inside the main channel by a single set of fins extending radially between the external surface of the inner tube and the internal surface of the tubular element or a distal added tubular body, said set of fins being on the side of the distal end of the tubular element, said fins being absent in the zone of the deflected jets,
- the inner tube is held in coaxial position inside the main channel by two set of fins extending radially between the external surface of the inner tube and the internal surface of the tubular element and/or an added tubular body, a first set of fins being on the side of the tubular element proximal end and a second set of fins being on the side of the tubular element distal end, said fins being absent in the zone of the deflected jets,
- the fins and the inner tube form a single-piece part inserted into the tubular element or into the tubular body itself inserted into the tubular element,
- the proximal end of the inner tube is at the level of the distal outlet orifice(s) of the auxiliary channel(s),
- the proximal end of the inner tube is at the level of the proximal end of said respiratory assistance device,
- the proximal end of the inner tube stands back from the proximal end of said respiratory assistance device, inside the main channel,
- the deflection means are configured so as to allow turning the jets towards the distal end of the tubular element according to an incidence with respect to the central axis of said tubular element, and hence with respect to the coaxial inner tube, comprised between 90°, the axis of the jets being perpendicular to said central axis, and 25°, the axis of the jets crossing the central axis according to an angle of 25°,
- the inclination of the deflected jets is different of 90° with reference to the central axis of said tubular element, the deflected jets being not radial but inclined towards the distal end and the centre of the main channel, and the proximal end of the inner tube is at the level of the distal outlet orifice(s) of said auxiliary channel(s), the deflection means allow making the jets of breathable gases of the auxiliary channels converging towards each other, inside the main channel, all the jets have the same incidence, the jets have different incidences according to the outlet orifices, the incidence of the jets is of about 45°, the single-piece part with fins and inner tube is introduced into the tubular element through the proximal end of the latter, the fins being arranged only on the side of the proximal end of said tubular element and moreover forming an obstacle to a clogging of the main channel, the obstacle to the clogging of the main channel does not prevent the potential passage of a probe, for example suction, measurement or sampling probe, the single-piece part with fins and inner tube includes at the radial periphery of the fins, in particular for each set of fins, a circular ring whose external surface is in contact with the internal surface of the tubular element or an added tubular body, the single-piece part with fins and inner tube includes at the radial periphery of the fins, in particular for each set of fins, a circular ring whose external surface is in contact with the internal surface of a tubular body inserted into the tubular element, the tubular element includes structural elements intended to form alone or in combination with other structural elements of the circular ring or of the tubular body, in part or in totality, at least the auxiliary channel(s), the tubular body includes structural elements intended to form alone or in combination with other structural elements of the tubular element, in part or in totality, at least the auxiliary channel(s), the circular ring of the single-piece part or the tubular body includes structural elements intended to form alone or in combination with other structural elements of the tubular element, in part or in totality, the auxiliary channel(s) and a part of the outlet orifice(s) of the auxiliary channels, the circular ring is of reduced thickness, in the case of a single-piece part with fins, inner tube and circular ring arranged at the proximal end of the tubular element, said circular ring is of such length that its distal end ends up before or just at the distal outlet orifice(s) of the auxiliary channel(s), the circular ring, in the case of a single-piece part arranged on the side of the proximal end of the tubular element, includes structural elements intended to form alone or in combination with other structural elements of the tubular element, in part or in totality, at least the auxiliary channel(s), the single-piece part with fins and inner tube includes at the radial periphery of the fins a circular ring whose external surface is in contact with the internal surface of the tubular element, said circular ring being of such a length that its distal end ends up at the distal outlet orifice(s) of auxiliary channel(s), and the circular ring includes structural elements intended to form alone or in combination with other structural elements of the tubular element, in part or in totality, at least the auxiliary channel(s), the distal outlet orifice(s) of the auxiliary channel(s) are individual and punctual, the diameter of each punctual outlet orifice is lower or equal to 150 micrometres, the diameter of each punctual outlet orifice is lower or equal to 100 micrometres, the diameter of each punctual outlet orifice is comprised between 50 micrometres and 10 micrometres and is preferably of about 25 micrometres, the diameter of each punctual outlet orifice is comprised between 20 micrometres and 5 micrometres and is preferably of about 10 micrometres, the diameter of each punctual outlet orifice is comprised between 150 micrometres and 10 micrometres, the diameter of each punctual outlet orifice is comprised between 150 micrometres and 100 micrometres, the auxiliary channels have, over at least a part of their travels, a diameter substantially equal to that of their outlet orifices, a given auxiliary channel emerges through a single outlet orifice, a given auxiliary channel emerges through several outlet orifices, the outlet orifices are at their distal ends of the auxiliary channels, the outlet orifices are offset with respect to the distal ends of the auxiliary channels, said distal ends of the auxiliary channels beyond outlet orifices being dead ends, the diameters of the outlet orifice and of the corresponding auxiliary channel are identical, at least the distal part(s) of the auxiliary channel(s) emerging into the main channel is/are parallel to the latter, the outlet orifice of the auxiliary channel is in a recess of the internal wall of the tubular element, said recess forming deflection means, the auxiliary channel(s) are arranged in the wall of the tubular element, the device includes several auxiliary channels, each auxiliary channel forming a tubular passage in the wall of the tubular element, the device includes a single common auxiliary channel to which the outlet orifice(s) are connected, said common auxiliary channel being an annular passage or a distribution ring, which is external and substantially coaxial and parallel to the central axis of said tubular element, at least certain of the outlet orifices are connected to each other, forming a single outlet orifice in the form of an annular band or a ring segment and whose width/thickness of opening/orifice corresponds to the diameter of an individual punctual orifice, i.e. a width/thickness lower than 150 microns, in the case of a single auxiliary channel forming an annular passage coaxial to the main channel, the outlet orifices are connected to each other, forming a single annular outlet emerging into the main channel, the annular outlet having a width/thickness corresponding to the diameter of an individual punctual orifice, the outlet orifices are chosen among individualized punctual orifices and/or outlet orifices connected to each other into a preferably annular or semi-annular band-shaped opening/orifice, the device includes one annular band-shaped outlet orifice of auxiliary channels, the device includes several semi-annular band-shaped outlet orifices of auxiliary channels, the distal outlet orifice(s) of the auxiliary channel(s) are semi-annular bands of reduced thickness, the distal outlet orifice(s) of the auxiliary channel(s) are in practice an outlet orifice in the form of an annular band of reduced thickness along the internal circumference of the tubular element, the thickness of each annular or semi-annular band-shaped outlet orifice is lower than 150 micrometres, the thickness of each annular or semi-annular band-shaped outlet orifice is comprised between 50 micrometres and 10 micrometres and is, preferably, of about 25 micrometres, the device includes, in addition to the semi-annular band-shaped outlet orifice(s), individualized punctual outlet orifices, the device includes, in addition to the semi-annular band-shaped outlet orifice(s), punctual outlet orifices, said punctual orifices having a diameter lower than 150 micrometres, the band-shaped outlet orifice(s) result from the connection of at least certain of the distal outlet orifices and of their corresponding auxiliary channels, the concerned auxiliary channels being hence annular or semi-annular band-shaped, in the case where the outlet orifice(s) are annular or semi-annular band-shaped, the circular ring of the single-piece part including structural elements intended to form alone or in combination with other structural elements of the tubular element, in part or in totality, at least the auxiliary channel(s), moreover forms a part of the outlet orifice(s) of the auxiliary channels, the circular ring including structural elements intended to form alone or in combination with other structural elements of the tubular element, in part or in totality, at least the auxiliary channel(s), moreover forms a part of the outlet orifice(s) of the auxiliary channels, in the case where the outlet orifice(s) are annular or semi-annular band-shaped, the tubular body including structural elements intended to form alone or in combination with other structural elements of the tubular element, in part or in totality, at least the auxiliary channel(s), moreover forms a part of the outlet orifice(s) of the auxiliary channels, the tubular body including structural elements intended to form alone or in combination with other structural elements of the tubular element, in part or in totality, at least the auxiliary channel(s), moreover forms a part of the outlet orifice(s) of the auxiliary channels, the distal outlet orifice(s) of the auxiliary channel(s) are punctual and/or annular or semi-annular band-shaped, and the diameter of the punctual orifices or the thickness of the band-shaped orifices is lower than 150 micrometres, in the case of connected outlet orifices, the corresponding auxiliary channels are also connected to each other, forming an annular or semi-annular auxiliary channel over the totality of their lengths or only a part, the distal jet outlet orifice is formed in a first face moving away from said main channel and the deflection means are formed by an inclined, second face of said main channel, arranged opposite said first face and converging towards the outlet orifice, the first face is on the tubular element, the second face is on the tubular element or on the tubular body, the terminal portion of the main channel on the distal end side is flared, the second face is extended towards the distal end of the main channel by a wall slightly flaring said main channel, the deflection means are formed directly in the internal wall of the tubular element, the deflection means are formed on a tip added at the distal end of the tubular element, the deflection means consist in a discontinuous set of generally conical recesses, formed in the internal wall, and at the bottom of each of which emerges the distal end of an auxiliary channel through the outlet orifice thereof, the device includes a plurality of auxiliary channels, at least some of which are fed in common with pressurized breathable gas, the auxiliary channels not fed in common serve for the introduction of additional gaseous products, such as medicine products or humid gases, at least one part of the auxiliary channels are fed in common with breathable gas through a distribution ring, coaxial to the tubular element, at least another part of the auxiliary channels are fed in common with medicine products or humidity, the terminal portion of the main channel on the distal end side includes a narrowed part, the terminal portion of the main channel on the distal end side includes a narrowing ring, the distal end of the inner tube is at the distal end of said respiratory assistance device, the distal end of the inner tube stands back from the distal end of said respiratory assistance device, inside the main channel, the distal end of the inner tube is made at a determined distance from the zone of arrival on the inner tube of the axes of the deflected jets exiting directly from the orifices, said determined distance being of at least 5 mm, the distal end of the inner tube is made at a determined distance from the zone of arrival on the inner tube of the axes of the deflected jets exiting directly from the orifices, said determined distance being of at least 10 mm, the distal end of the inner tube is made at a determined distance from the zone of arrival on the inner tube of the axes of the deflected jets exiting directly from the orifices, said determined distance being of at least 15 mm, the distal end of the inner tube is made at a determined distance from the zone of arrival on the inner tube of the axes of the deflected jets exiting directly from the orifices, said determined distance being more particularly of 16 mm, the inner tube has a length of about 33.5 mm, the inner tube has more particularly a length of about 43.5 mm, the fins have lengths lower than the length of the inner tube, the distal end of the inner tube is approximatively at the distal end of said respiratory assistance device and the proximal end of the inner tube is approximately at the proximal end of said respiratory assistance device, in the respiratory assistance device, the transverse distance between the outlet orifices of auxiliary channels and the external surface of the inner tube is comprised between 1 mm and 5 mm, the outlet orifices of auxiliary channels are arranged into a crown, the device includes at least one crown of outlet orifices of auxiliary channels, the outlet orifices of a crown being arranged along a cross-section of said tubular element, the device includes at least two crowns of outlet orifices of auxiliary channels offset along said tubular element, the outlet orifices of different crowns coming from identical auxiliary channels, wherein a same auxiliary channel can emerge through several outlet orifices, the device includes at least two crowns of outlet orifices of auxiliary channels offset along said tubular element, the outlet orifices of different crowns coming from different auxiliary channels, a given auxiliary channel emerging only through a single outlet orifice, the outlet orifices of a crown or a part of these latter are connected to form a common annular or semi-annular orifice, the device includes at least two crows of annular or semi-annular band-shaped outlet orifices;

the device with crowns of orifices includes, in addition to its annular and/or semi-annular band-shaped outlet orifice(s), punctual outlet orifices, the jets have different incidences according to the crown of outlet orifices, the device includes a pressure gauge connected to the main channel to measure pressure, the point of measurement of pressure of the pressure gauge connected to the main channel is located towards the distal end of the device, the point of measurement of pressure of the pressure gauge connected to the main channel is located towards the proximal end of the device, the device includes a pressure gauge connected to the inner duct of the hollow, by-passing and jet-breaking tube, the device includes internally a visual indicator of direction and strength of the gaseous flow passing through the device, said indicator is in the main channel of the device, said indicator is located towards the distal end of the device, said indicator is located towards the proximal end of the device, said indicator is an element turning in the direction of the gaseous flow, said indicator is a flexible element turning in the direction of the gaseous flow and deforming itself as a function of the force of the gaseous flow, said indicator is a flexible strip made of plastic material, fastened at one of its two ends to a holding fin of the inner tube, when the gaseous flow is expiratory, the strip is turned towards the proximal end of the device and, as a function of its length, may exit therefrom through said proximal end, and/or, in some variants:

the device is of the dual opposite flow type, making it possible to favour the breathing out as well as the breathing in of a patient, the device including at least one additional auxiliary channel, independent of the first auxiliary channel(s) of the jets of the main channel distal end, and connected to a source of pressurized gas, said at least one additional auxiliary channel emerging into the main channel in the vicinity of the proximal end of the latter, whereas, opposite each outlet orifice of the corresponding additional auxiliary channel, are provided means for the deflection of the gas jet passing through the latter towards the inside of said main channel, in order to form jets of proximal end of the main channel, and the two zones of deflected jets corresponding respectively to the jets of the main channel distal end and to the jets of the main channel proximal end each include a jet-breaking and by-passing inner tube, wherein said inner tube can be extended so as to be unique and common to the two zones or each of the zones includes its own inner tube, at least the end(s) of said additional auxiliary channel(s) emerging through respective outlet orifices into the main channel is/are parallel to the latter, preferably, in the case of a dual flow device with an additional auxiliary channel, the proximal part of the device is similar, if not identical, symmetrically, to the distal part of said device, at least as regards the arrangement of said auxiliary channels and said deflection means, the device forms the air in and out tip of a respiratory assistance mask intended to be applied to the visage of a patient, the device forming the air in and out tip of a respiratory assistance mask is removable, and/or, in some variants:

the device further includes by-passing means adapted to by-pass a fraction of volume of said breathable gas intended to said auxiliary channel before the entry thereof in the latter, and ambient air suction means driven by said by-passed fraction of breathable gas and said suction means are connected to the main channel so that the suction means are adapted to lead, into said main channel, the sucked ambient air mixed with said by-passed fraction of breathable gas, the device includes means for adjusting the fraction of breathable gas by-passed by said by-passing means, the means for adjusting the fraction of by-passed breathable gas are arranged between said by-passing means and the ambient air suction means, the means for adjusting the fraction of by-passed breathable gas include at least one gate, the device further includes means for regulating the flow rate of diluted breathable gas exiting from said suction means and intended to enter said main channel, the means for regulating the flow rate of diluted breathable gas are arranged between said ambient air suction means and fluidic communication means, the means for regulating the flow rate of diluted breathable gas include at least one gate, the flow rate of diluted breathable gas exiting from said suction means pass into the main channel through a communication orifice that is formed in the wall of said device, the main channel is formed by a tube, the main channel is formed by a flexible tube, the flow rate of diluted breathable gas exiting from said suction means pass through a tight flexible sheath that surrounds, at least over one part of its length, said flexible tube forming the main channel and that forms a peripheral path about said flexible tube and into which the communication orifice emerges, the suction means are mounted directly onto said flexible tube, in the vicinity of its proximal end, the communication orifice is arranged between the means for deflecting the jets and the distal end of the main channel, the communication orifice is divided into multiple communication orifices, and/or, in some variants:

the device further includes means for braking the exit of the breathing-out gases of the patient, the device further includes means for braking the entry of breathing-in gases from the outside to the patient, the braking means are arranged on the proximal side of the device, the braking means are integrated to the device,
the braking means are added by connection to the proximal end of the device,
the braking means include valves,
the braking means are configured so as to brake the passage of the gases only during at least a determined breathing in and/or breathing out phase and preferably during a breathing-in phase that is the beginning of the breathing in, in order to cause an intrathoracic depression favourable to the venous return towards the heart,
the device further includes means for braking the entry of breathing-in gas from the outside to the patient and the braking means are configured so as to brake the passage of the gases only during a breathing-in phase that is the beginning of the breathing in, in order to cause an intrathoracic depression favourable to the venous return towards the heart,
the device further includes means for the spontaneous braking of the entry of external air into the main channel via its proximal end,
the means for braking the entry of external air into the main channel include a hollow body provided with a first and a second normally-closed valves, the first valve being adapted to open spontaneously and immediately during an overpressure/counter-pressure coming from the patient airway, in particular during a thoracic compression, whereas the second valve is adapted to open spontaneously, but progressively, outside said overpressure/counter-pressure, in particular during the cancelling of a thoracic compression, and the hollow body is arranged at the proximal end of the tubular element of the device,
the first and second valves are arranged in parallel between the outside and the internal cavity of the hollow body,
the first and second valves are arranged in series between the outside and the internal cavity of the hollow body, one of said valves being carried by the other,
the first valve is consisted by an elastic membrane applying spontaneously against a seat provided inside said hollow body and is linked to said seat by fastening points distributed over its periphery, the air expelled during overpressure/counter-pressure passing freely from the cavity of the hollow body to the outside through passages that are formed spontaneously and immediately by the elastic deformation of said membrane between said fastening points and said seat, and the second valve is formed by at least one slot with jointed edges formed in said membrane, the air sucked during the cancelling of the overpressure/counter-pressure passing progressively by being braked from the outside to the cavity of the hollow body through the passage that is formed spontaneously in said membrane by elastic deformation of the latter, causing the progressing spacing apart of its joined edges,
the means for braking the entry of external air into the tubular element of the device are integral part of the latter,
the means for braking the entry of external air into the tubular element of the device are removably added to the latter,
and/or, in some variants:
the tubular element forming the main channel of the device includes at least one lateral orifice of security that passes through its lateral wall at least substantially opposite the point of convergence of the axes of the jets of breathable gas(es) and that is adapted to connect to the outside the part of said main channel that is on the distal/downstream side with respect to the direction of the jets of breathable gas(es) and with respect to the deflection means,
the distal part of the main channel is in direct communication with the exterior, through said lateral orifice of security,
the lateral orifice of security is closed by a removable plug,
the lateral orifice of security is closed by an impossible-to-loose removable plug,
the lateral orifice of security is closed by a calibrated exhaust valve opening in case of overpressure,
the device includes fibrous or porous means to mask the noise of the jets of respiratory gas passing through said lateral orifice of security,
the device includes a duct connecting the lateral orifice of security to the outside,
the fibrous or porous means are in the duct,
the duct is consisted by a coaxial duct surrounding the tubular element,
the coaxial duct emerges to the outside on the side of the proximal end of said tubular element,
the coaxial duct emerges to the outside on the side of the distal end of said tubular element,
the duct is consisted by a flexible sheath surrounding the tubular element and emerging to the outside on the side of the proximal end of said tubular element,
the duct is consisted by a flexible sheath surrounding the tubular element and emerging to the outside on the side of the distal end of said tubular element,
the proximal part of the main channel includes protruding internal obstacles preventing the tight plugging of the proximal end,
and/or, in some variants:
so that the device can deliver to the patient airway a predetermined flow rate of respiratory gas(es) under a working pressure whose value must be comprised in a range of working values to ensure the efficiency of said device without endangering said patient, said device being connected to the source of respiratory gas(es) by a gas feeding duct and at a feeding pressure comprised between a minimum value and a maximum value, the respiratory gas feeding duct includes an specific load-loss element ensuring that said working pressure is at most equal to the higher value of said range of working values, when said feeding pressure is at said maximum value,
the specific load-loss element is consisted by a plug adapted to plug the respiratory gas feeding duct and pierced with a longitudinal passage for the gas(es),
the value of the load loss added by said specific load-loss element is adjusted by the length of the pierced plug,
the specific load-loss element is consisted by a profile segment,
and/or, in some variants:
the device includes between the deflection means and the distal end of the main channel, communication means controllable in opening and closing and adapted, when they are in open position, to form a passage connecting said main channel to the external environment,
the passage connecting the main channel to the external environment has a variable section,
the communication means are of the laterally pierced rotary ring type, adapted to clear passages of different diameters,
the rotary ring is mounted directly on the tubular element, the rotary ring is mounted on a chimney in communication with the main channel,
and/or, in some variants:
the device further includes at least one feeding duct fed with a liquid product to be nebulized into the main channel and nebulization means,
the device further includes at least one added feeding duct fed with a liquid product to be nebulized and housed in the main channel, said feeding duct entering the main channel through the proximal end of the tubular element and emerging into said main channel in the vicinity of the emergence, into the latter, of the outlet orifice(s) of the auxiliary channel(s),
the internal diameter of said added feeding duct is of the order of 200 to 300 micrometres,
outside the tubular element, the added feeding duct is ascending and at least approximately perpendicular to the axis of the tubular element,
the feeding duct is removably added to the tubular element,
the feeding duct is moreover fastened to the tubular element by means of a clamp arranged astride on the edge of the proximal end of the tubular element,
the distal-side end of the added feeding duct has the shape of a bevel,
the distal-side end of the added feeding duct is on the vicinity of the deflection means,
the added feeding duct includes a plurality of independent distal feeding orifices,
the added feeding duct includes a plurality of independent channels,
and/or, in some variants:
a gas feeding duct connects the auxiliary channel(s) of the device to the source(s) of breathable gas(es), said gas feeding duct including on the side of the source (s), a load-loss device adapted to limit the flow rate and the pressure of said breathable gas available at the exit of said source and to impose to said jet of breathable gas predetermined values of flow rate and pressure and, on the side of the auxiliary channel(s), includes a calibrated exhaust valve adapted to place said gas feeding duct in communication with the atmosphere as soon as the pressure in said gas feeding duct exceeds said predetermined pressure value,
the load-loss device is adjustable so as to allow imposing to the jets of breathable gas a plurality of predetermined or preset values of flow rate and pressure,
the calibration of the calibrated exhaust valve is adjustable,
the load-loss device is incorporated to the tubular element,
the load-loss device is external to the tubular element,
the calibrated exhaust valve is incorporated to the tubular element,
the calibrated exhaust valve is external to the tubular element,
the device includes a humidifier in the gas feeding duct connecting the source(s) of breathable gas to the auxiliary channel(s),
the humidifier is arranged between the load-loos device and the calibrated exhaust valve,
and/or, in some variants:
the device includes a controlled gate liable to plug at least partially the proximal end of the main channel at least during the insufflation of the breathable gas,
the controlled gate forms a monolithic unit with the tubular element,
the controlled gate is added to the tubular element,
the controlled gate is integral with a tip liable to be nested on the proximal end of the tubular element,
the controlled gate includes a tight enclosure of toroidal section, arranged in the vicinity of the proximal end of the main channel and including at least one flexible and elastic internal wall that, by expanding or retracting in response to the introduction or evacuation of an inflating fluid in said tight enclosure, controls the section of passage of said main channel,
the free edge of the proximal end of the tubular element includes at least one indentation,
the device includes at least one pressure tap arranged on the side of the distal end of the tubular element,
the pressure tap includes an annular peripheral chamber coaxial to the tubular element and emerging on the distal side of the device through a distal annular passage, said annular peripheral chamber being in relation with a lateral outlet tip,
an annular, fibrous or porous, filter is arranged in the annular peripheral chamber,
the pressure tap is formed by the outlet orifice through which one of the auxiliary channels formed in the wall of the tubular element emerges in the vicinity of the distal end of said tubular element,
the device includes means receiving the pressure taken through said pressure tap and liable to impose the opening to the controlled gate to clear the main channel,
the device includes a calibrated exhaust gate arranged at the proximal end of the tubular element, of the opposite side of the free edge of the proximal end with respect to said controlled gate,
the introduction and the evacuation of the inflating fluid into/from said tight enclosure results from the bidirectional displacement of a suitable volume of fluid contained in a buffer capacity having a controllable variable volume,
the inflating fluid is a gaz.

The invention also relates to a nasal respiratory assistance apparatus for a patient, including a device according to the invention for each nostril, the two devices being fed with breathable gas(es) in parallel, each device including a tubular element forming a main channel that is intended to be connected by its distal end to the respiratory system of the patient through one of his nostrils, said main channel connecting the respiratory system of said patient to the outside by its proximal end, said device further including at least one auxiliary channel allowing the injection of jets of breathable gas(es) intended for the ventilation of said patient through distal outlet orifices of the auxiliary channels, said outlet orifices emerging into said main channel in the vicinity of the distal end of the latter, deflection means allowing the deflection of the jets of gas towards the inside of said main channel, and it includes for each of the devices a jet-breaking and by-passing inner tube.

In various embodiments of the apparatus, the following means, which can be used alone or in any technically possible combination, are used:
the device incorporated to the apparatus has one or several described characteristics relating to said device,
the apparatus includes a monolithic part incorporating two devices according to the invention,
in the monolithic part, the two tubular elements are parallel to each other, the apparatus further includes a means for feeding a liquid to be nebulized in the gaseous flow passing through the apparatus towards the patient, the apparatus includes, in relation with each tubular element, two parts of different diameter arranged in series, the part with the greatest diameter being proximal, i.e. on the free-air side opposite to the patient side, and being provided with a lateral tubular fitting, the part of greatest and smallest diameters are separated by a conical intermediate part, the apparatus includes, for each part of greatest diameter, a sleeve arranged in said part of greatest diameter and providing therein a space of annular section, the lateral tubular fitting emerging into said annular-section space, means for fastening the sleeve to said part of greatest diameter plugging said annular-section space on the proximal side opposite to a conical intermediate part connecting the proximal, greatest diameter part to the smallest diameter part, the apparatus includes for each conical intermediate part a lateral liquid feeding duct emerging into said conical intermediate part, in the vicinity of the connection of the latter with the smallest diameter part, each lateral feeding duct protrudes inside said conical intermediate part and has a bevel whose inclination is opposite to that of said conical intermediate part, at the place where said lateral duct emerges, the apparatus is provided with a breathable gas feeding device, associated with a source of such gas(es) and provided with a pressure detector adapted to detect the beginning of the breathing out actions and the beginning of the breathing in actions of the ventilated patient, said feeding device further including, fed in parallel by said source, calibration means permanently delivering a flow of breathable gas(es) under a first pressure adapted to keep open the bronchioles of said patient, by avoiding the collapse, and a calibrated controllable gate to deliver, when it is open, a flow of breathable gas(es) under a second pressure, higher than said first pressure and adapted to efficiently assist the breathing in of said patient, said controllable gate being controlled by said pressure detector, at the closure during the breathing out actions and at the opening during the breathing in actions, the feeding device includes a flowmeter interposed between the calibration means and the controllable gate, on the one hand, and the auxiliary channels, on the other hand, the feeding device includes an alarm device controlled by the pressure detector, a pressure tap for the detector emerges into at least one of the downstream tubular elements, on the distal side, i.e. on the patient side, said deflection means and in the vicinity of the distal end of said tubular element, said pressure tap being connected to the detector by a connexion tube, the pressure tap is a hole passing through the wall of the tubular element and the connection tube is external to the latter, the connexion tube is arranged inside the tubular element and the pressure tap is formed by a lateral indentation, formed in the connexion tube and having a length equal to several times the diameter of said connexion tube, the apparatus includes mobile members adapted to restrict the section of passage of the gaseous jets at the deflection means, the mobile members are consisted by the distal ends of bushes able to slide with strong friction inside the main channels, the apparatus includes, on each of its two distal ends, an externally-added flexible nostril sleeve, intended to come into contact with the internal wall of the corresponding nostril, each nostril sleeve includes an opening opposite the distal opening of the tubular element, each nostril sleeve is made of an open-cell foam material and plugs the distal opening of the distal end of the tubular element, while ensuring the passage for the breathable gas(es) and for the possible nebulized liquids.

The invention also relates to a respiratory assistance mask provided with a device according to the invention. The device in relation with the mask has one or several of the described characteristics relating to said device.

BRIEF DESCRIPTION OF THE DRAWINGS

The present invention will now be exemplified, without being limited thereby, by the following description in relation with the following figures:

FIG. 6 shows, in a schematic and partial axial sectional view, a dual opposite flow variant of the device according to the present invention, FIG. 7 shows, in an axial sectional view, a variant embodiment of the device of the invention, FIGS. 8, 9 and 10 are cross-sectional views of the device of FIG. 7 along the lines III-III, IV-IV and V-V, respectively, FIG. 11 shows, in an axial sectional view, a schematic view of a part of the device of the invention according to a first embodiment of the jet-breaking and by-passing inner tube.

DETAILED DESCRIPTION OF THE PREFERRED EMBODIMENTS

In its principle, the device of the invention is hence consisted of a tubular element, generally a tube, that forms a main channel and that is intended to be connected by its distal end to the airway of the patient whereas the proximal end of the tubular element emerges into free air outside the patient, the respiratory system of the patient being hence connected to the outside through the main channel of the device. Auxiliary channels are formed in the thickness of the tubular element and emerge in the main channel. The auxiliary channels are fed with respiratory gas(es) through a feeding duct. The device includes deflection means to make converging towards each other, inside the main channel, the jets of respiratory gas(es) injected through said auxiliary channels towards the main channel. Preferably, the means for deflecting the jets of breathable gas(es) deflect the jets towards the central axis of the main channel.

Figure 1:
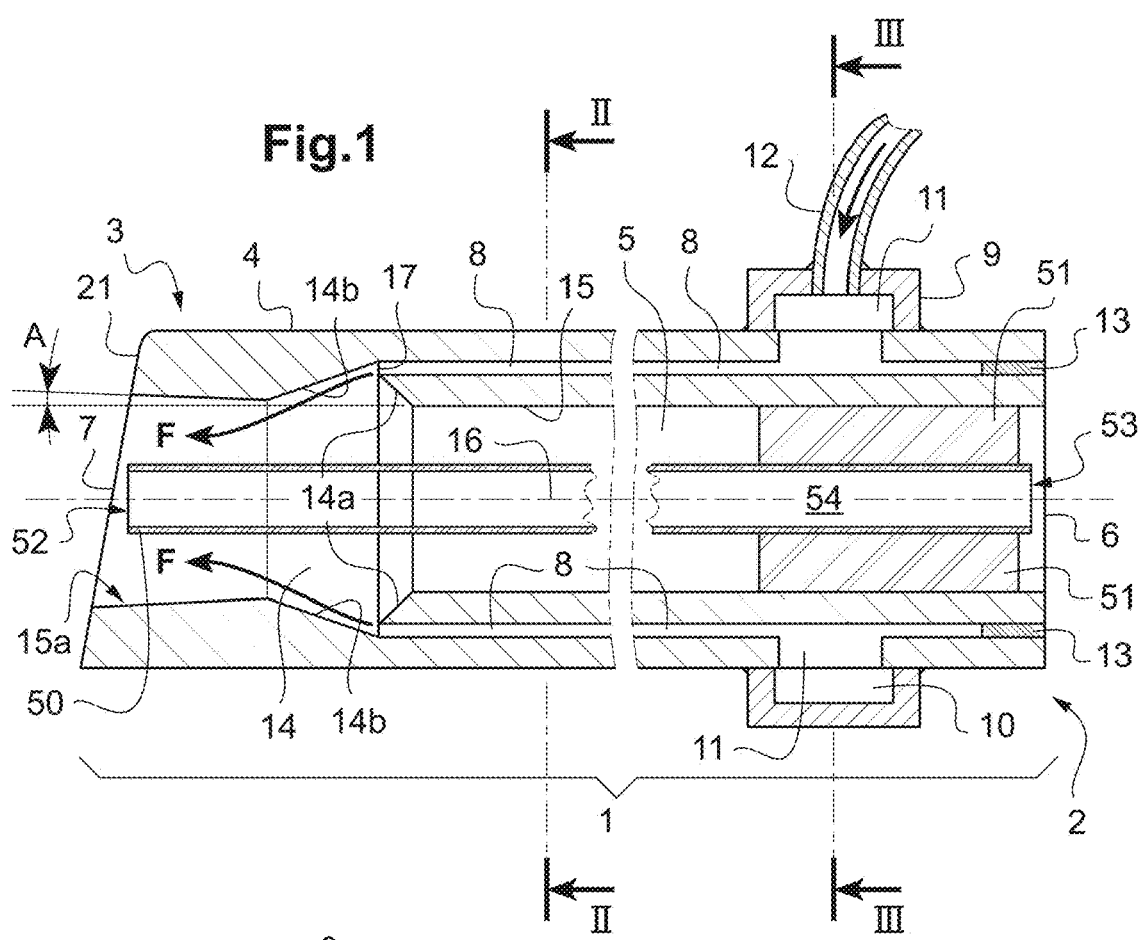
FIG. 1 is a schematic and partial view, in enlarged axial section, of a first embodiment of the device of the invention.

In FIG. 1 schematically shows, in a large-scale view, the tubular element with its proximal 2 and distal 3 ends of an embodiment 1 of the device according to the invention. This embodiment may constitute or be combined to, for example, a facial mask, a laryngeal mask, a pharyngeal mask, a nasal adapter, an endotracheal probe, an oronasal probe, with or without cuffs, a paediatric endotracheal probe, a gas monitoring probe, an endobronchial probe, a nasopharyngeal probe, a anatomic intubation probe for children, a neonatal Cole probe, a Guedel tube probe, or an oxygen therapy nasal probe. The device of the invention may be used in any position, extracorporeal or intracorporeal, and in particular supraglottic or supratracheal.

In fact, the field of application of the invention is very wide: invasive or non-invasive ventilation, adult or paediatric, in particular: Boussignac type CPAP valve, mono-jet CPAP, CPAP specific to the use for sleep apnoea, valve for cardiac arrest, and as a varied interface: mask/laryngeal mask/oxygen spectacles/probe, etc.

The device 1 includes a flexible tubular element 4, in particular to fit the patient's morphology, delimiting a main channel 5 emerging, through the proximal orifice 6, at the proximal end 2, and through the distal orifice 7, at the distal end 3. In a variant, the tubular element 4 is preformed and rigid.

Hence, the main channel 5 is capable of ensuring the passage between the orifices 6 and 7, one of which, the distal orifice 7, is intended to be inside the airways of a patient or outside, in relation with these latter, and the other one, the proximal orifice 6, is intended to be in communication with the external environment of said patient. This proximal orifice 6 may emerge to free air and, in this case, the patient may breath in free air and breath out the vitiated air through the main channel 5. The proximal orifice 6 may also be connected to at least one source of pressurized breathable gas(es) (not shown) and a system of unidirectional valves may be provided so that the patient breathes in the breathable gas(es) from said source through said main channel 5 and breathes out the vitiated gas to free air, also through this main channel 5.

The diameter of the main channel 5 is of the order of a few millimetres. Satisfying tests have been performed with diameters of 3 mm, 7 mm and 8 mm, or even slightly more.

Moreover, in the thickness of the wall of the tubular element 4 are formed auxiliary channels 8, extending over the almost totality of the length of the main channel 5. These auxiliary channels 8 are intended to be connected to one (or several) sources of pressurized breathable gas (not shown). For example, this pressure is of a few bars, for example 1, 2 or 4 bars, and it is adjustable. Preferably, as shown, these auxiliary channels are individualized channels over at least a part of their travels. In variants, the auxiliary channels have a common part forming a circular chamber coaxial and external to the main channel or are reduced as regards their individual travel to the outlet orifices emerging into the main channel, and in this latter case, it may be considered that there is only one auxiliary channel. In any case, the auxiliary channel(s) emerge into the main channel through several outlet orifices to form therein jets of breathable gas(es).

Figure 3:
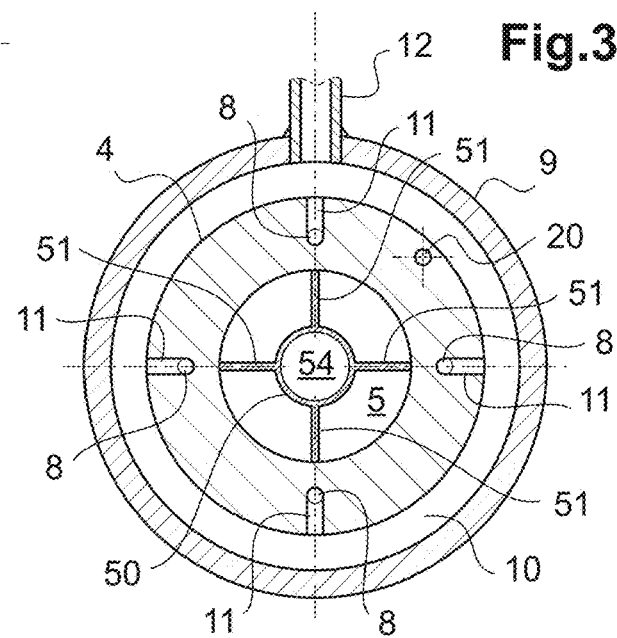

As shown in FIGS. 1 and 3, the connection to the source(s) of pressurized breathable gas(es) may be performed by means of a ring 9, tightly surrounding the tubular element 4, on the side of the proximal end 2, and delimiting a tight annular chamber 10 about said tubular element. The auxiliary channels 8 are placed in communication with the chamber 10 thanks to local tearings 11 of the wall of the tubular element 4 and said chamber 10 is connected to the sources of breathable gas(es) by a link 12. Of course, the proximal ends of the auxiliary channels 8 are plugged, for example by plugs 13. The auxiliary channels 8 have a smaller diameter than that of the main channel 5.

On the distal side, each of the auxiliary channels 8 emerges through a respective outlet orifice 17 into a recess 14 of the internal wall 15 of the tubular element 4. The recess 14 is annular and centred to the central axis of revolution 16 of the tubular element on the distal end 3. It has a face 14a, substantially transverse or slightly inclined so as to constitute a flaring of the main channel 5, in which emerge said auxiliary channels 8 through their outlet orifices 17, as well as face 14b following the face 14a and converging in the direction of the axis 16.

Preferably, between the converging inclined face 14b and the distal orifice 7, the internal wall 15 has a part 15a slightly flared towards the outside, as illustrated by the angle A in FIG. 1.

Hence, when the auxiliary channels 8 are fed with pressurized breathable gas(es) through the elements 9 to 12, the corresponding gaseous jets hit the inclined face 14b, which deflect them towards the axis 16 (arrows F in FIG. 1), hence forming deflection means, and generating in the vicinity of the latter a zone of depression favouring the gaseous circulation inside the main channel 5, from the proximal orifice 6 towards the distal orifice 7. The breathing in of the patient is then favoured.

It is understood that the auxiliary channels can be made within the device in a manner different from that shown by way of example. Hence, for example, the auxiliary channels may be tearings 11 or grooves over their whole lengths rather than continuing in channels embedded in the wall of the tubular element as shown, said tearings being externally closed by an added tubular external wall applying on the tubular element. Said tubular external wall may also form deflection means at the outlet orifices of the auxiliary channels. Said auxiliary channels may also be made between the internal wall 15 of the tubular element 4 and the external wall of a tubular body (denoted 55 in FIGS. 7 and 10), a single-piece part with an inner tube and fins further inserting into the tubular body 55, the tubular element 4 and/or the tubular body 55 including structural elements adapted for that purpose. As a variant, a circular ring belongs to the single-piece part and this is this circular ring that is inserted directly into the tubular element, the circular ring then acting as the tubular body. In other variants with a single-piece part having a circular ring, the circular ring of the single-piece part is inserted in the tubular body, the latter being inserted into the tubular element (see FIGS. 12, 13).

It is understood that it is implemented a circular ring, i.e. which forms a complete circle essentially for reasons of mechanical strength. If the matter of the single-part piece is strong enough, it may be contemplated that the ring in question is discontinuous, in arcs, at the peripheral ends of the fins.

Preferably, the distance between each of the outlet orifices 17 of the auxiliary channels 8 and the distal orifice 7 is of the order of 1 to 2 cm.

Downstream the distal orifice 7, the pressure in the pulmonary cavity is low and almost constant.

As a variant, the distal orifices of the auxiliary channels forming the jets are semi-annular band-shaped orifices, or even a single annular or quasi-annular band-shaped orifice, instead of punctual. In the case of a single annular band-shaped orifice, it is understood that it may be in practice quasi annular, a few bridges of material linking the two edges of the band-shaped outlet orifice in order to better hold them at a determined distance between each other, distance that corresponds to the thickness of the band-shaped orifice.

Preferably, the punctual orifices have a reduced diameter and the band-shaped orifices have a reduced thickness, typically less than 150 μm as mentioned in the patent application PCT/FR2013 051979.

The inner tube 50 is arranged centrally in the main channel. The inner tube 50 is coaxial to the main channel 5, along the axis 16. The inner tube 50 is hollow, defining a lumen 54 and open at its two ends: a distal end 52 and a proximal end 53 that are oriented towards the corresponding ends and openings of same qualifier of the tubular element 4. The inner tube 50 is held in position thanks to fins 51 extended between the inner tube and the inner wall 15 of the tubular element 4. In a variant not shown in FIG. 1, a circular ring (shown in 56 in FIGS. 12, 13) is interposed between the internal wall 15 of the tubular element 4 and the fins 51, these latter being fixed to said circular ring. The fins have a reduced thickness so as not to cause, at the level thereof, a too important reduction of the gas circulation space in the main channel 5. Their number is also reduced, preferably comprised between one and four. In FIGS. 1 to 10, four fins are shown. The fins are arranged radially about the inner tube 50 and preferably equiangularly, i.e. for four fins at 90° from each other about the inner tube. The inner tube is substantially rigid. It may be contemplated that it is flexible but, in this case, the fins must extend along the inner tube in order that the latter follow at best the deformations of the tubular element 4 in case where the latter would also be flexible. Preferably, there is no fin in the zone of production of the jets, i.e. the zone of the outlet orifices of the auxiliary channels.

It is hence understood that the fins, herein arranged on the side of the proximal end of the tubular element, may be arranged at other positions and/or be more or less elongated and/or distributed into several sets of fins over the length of the main channel.

In the embodiment of the invention illustrated in FIG. 1, it has been indicated that the set of faces 14a and 14b was made by recessing 14 of the internal wall 15 of the main channel 5. That goes without saying that this embodiment is not limitative and that the faces 14a and 14b may be obtained in different manners. For example, in FIGS. 4 and 5, the face 14a is formed in the internal wall 15 of the tubular element 4, whereas the face 14b is provided on a tip 18 or 19 that comes and nests internally, tip 18, or externally, tip 19, to the tubular element 4, and in this case, the distal orifice 7 and the diverging wall 15a are carried by the corresponding tip 18 or 19.

In a variant embodiment of the recess 14, the deflection means do not form a continuous annular groove but are consisted by a discontinuous set of generally conical recesses, arranged in the internal wall, and at the bottom of each of which emerges through its outlet orifice the distal end of an auxiliary channel. The principle of operation of such a device is of course comparable to the above-described one.

Figure 2:
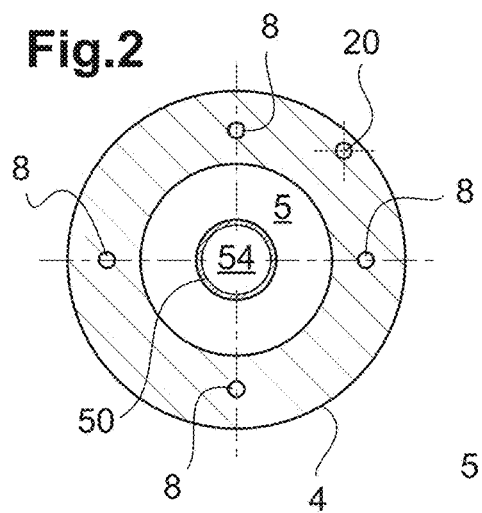
FIGS. 2 and 3 are cross-sectional views taken along the lines II-II and III-III, respectively, of FIG. 1, FIGS. 4 and 5 schematically illustrate, in enlarged axial sectional views, two variants embodiment for the distal end of the device according to the invention.

As shown in FIGS. 2 and 3, the auxiliary channels 8 are arranged regularly about the axis of the tubular element 4. The number is variable according to the uses (adult or child), but it is generally comprised between one and ten. Generally, the number of the outlet orifices of the auxiliary channels and the diameter of the outlet orifices and/or of the auxiliary channels are adjusted in order to allow a sufficient flow rate for the breathable gas(es). It is possible, for that purpose, to pick up the interest of the annular or semi-annular band-shaped outlet orifices that allow having a relatively wide outlet surface despite a thickness that may be low with respect to punctual orifices of small diameter that would be multiplied.

It can also be seen in these FIGS. 2 and 3 that the inner tube 50, with its internal lumen 54, is arranged centrally in the main channel 5 of the tubular element 4. In not-shown variants, the inner tube, while being parallel to the main axis of the main channel, is radially offset with respect to this axis of the main channel. The inner tube 50 is held in place by fins 51 that are seen in cross section in FIG. 3. In this example, four fins 51 are implemented, radially and equi-angularly arranged at 90° from each other about the inner tube 50. In this example, the fins directly come on the internal surface of the tubular element. Hollow guides for insertion and guiding of the fins may be made in the thickness of the internal surface of the tubular element to facilitate the insertion of the inner tube and of the fins thereof. Preferably, the inner tube and the fins thereof form a single-piece part. In variants, the single-piece part further include a circular ring to which the fins are connected and this is this circular ring that comes, by its external surface, on the internal surface of the tubular element. It can be provided an external snug on the circular ring and a hollow guide of the internal surface of the tubular element—or of a tubular body inserted in the tubular element—which are complementary, to facilitate the insertion of the single-piece part that includes this time also the circular ring. A locking means may be provided between the single-piece part and the tubular element or the tubular body.

It may be noted that the presence of fins 51 in the proximal end of the tubular element forms an obstacle preventing the accidental introduction of an object liable to tightly plug said proximal end.

In a variant, the inner tube is an individual element and wheel-shaped supports with fins serve to centrally maintain the tube. The supports with fins include towards the centre thereof an annular hub in which the tube is maintained and at the periphery thereof a circular ring of the previously mentioned type. These supports with fins have a reduced length (in the direction of the axis 16 of the tubular element) with respect to the previously described ones and several of them may be provided inside the main channel, for example a proximal side one, a median one and a distal side one of the tubular element for an elongated tube having a length close to that of the tubular element. In a variant, the supports with fins form with the inner tube a single-piece part and in this case, the annular hub may be omitted, the fins coming directly to the inner tube.

In FIGS. 1 to 5, the inner tube extends continuously between almost the two proximal and distal ends of the tubular element. It is however understood that the inner tube may be of lower length than the length of the tubular element, but in this case, it must be present at the deflected gas jets produced by the outlet orifices of the auxiliary channels so that its role of jet-breaker and of by-pass is effective. It is reminded that the inner tube is hollow and open at its two ends, it hence also serves as a by-pass, in particular for the gases breathed out by the patient. It results therefrom, in particular in case of haemoptysis, that the breathed-out blood may pass through the lumen 54 of the inner tube 50, which avoids that it is nebulized or atomized in the deflected jets.

It will be noticed that at least one of the auxiliary channels 8, instead of being connected in common with the other ones, to the source of pressurized breathable gas (through elements 9 to 12), may be continuously fed by the source of breathable gas, so as to maintain a positive pressure in the lungs of the patient, and that during or at the end of the breathing-out phase caused by the gas insufflation into the auxiliary channels 8 (anti-collapse effect).

According to still another variant of the invention, one of the auxiliary channels 8 may also be specialized to bring a medical flow or a humidification fluid, if the pressurized source have not the required characteristics.

To ensure the humidification, the auxiliary channel bringing water, preferably tepid, is preferably curved into a U shape at its distal end, and emerges into a cavity formed in the internal wall 15, cavity into which also emerges a channel bringing pressurized air. In said cavity, preferably located between the recess 14 and the distal orifice 7, the water channel and the air channel emerge opposite to each other, i.e. substantially on the same axis, the two fluids, air and water, arriving in opposite directions, which allows the atomization of the water, the steam obtained being then driven by the insufflated air.

At least one additional channel 20 may be provided in the thickness of the tubular element 4 in order to emerge into the distal end face 21 of the tubular element 4 and serve as a housing for a pressure measurement device (not shown).

When at least two pressure taps are present, in particular at each of the ends of the tubular element, they allow, thanks to the difference of the measured pressures, calculating the gaseous flow rate.

The tubular element 4 may include at the distal end 3 an inflatable cuff (not shown) provided with the required security devices or any other cuff allowing it to act as a security valve in case of overpressure in the lungs. This potential cuff may be inflated from an additional channel (not shown) associated with the tubular element 4.

Other security means intended to avoid a prejudicial overpressure in the airway of the patient may be implemented, in particular means for regulating the flow rate or the pressure of the breathable gases intended to be injected in the main channel of the respiratory assistance device. These means are one or several controlled gates and pressure measurement, decisional calculation and gate control devices. Moreover, it is also possible to implement means for introducing air from the environment. Indeed, the principle of the invention that consists in using a jet-breaking tube within a deflected jet device of the BOUSSIGNAC CPAP type may be implemented in all the applications of the deflected jet device of the BOUSSIGNAC CPAP type.

A security device may be simply constituted by an elastic sleeve surrounding the tubular element, partially bond to the latter, and covering a perforation formed through the wall of said tubular element, in particular in the vicinity of the proximal end. Hence, when the internal pressure becomes too high, the gas may flow through said perforation, then between the external wall of the tubular element and the internal wall of the elastic sleeve. If a security sleeve is also provided in the vicinity of the distal end, the corresponding perforation, placed beyond a potential friction-holding cuff, must put in communication the inside of the tubular element with the ambient air; said cuff must hence be bypassed, which is obtained for example by placing it around the elastic sleeve.

The dual-opposite-flow variant embodiment 22 of the device according to the invention, shown in FIG. 6, includes two devices 1.1 and 1.2, each having a structure similar to that of FIG. 1, which are inverted, placed side-by-side by their proximal ends, wherein the device 1.2 can be shorter than the device 1.1. In this variant embodiment 22, the distal orifice (on the patient side) of the device is consisted by the distal orifice 7.1 of the device 1.1, whereas the proximal orifice (on the side opposite to the patient) is formed by the orifice 7.2 of the device 1.2. Each of the devices 1.1 and 1.2 is provided with its pressurized breathable gas feeding system 9.1, 9.2, 10.1, 10.2, 11.1, 11.2 and 12.1, 12.2, feeding respective channels 8.1 or 8.2, emerging into annular recesses 14.1 or 14.2, close to said orifices 7.1 and 7.2, respectively. The device 22 forms a dual flow probe. This device being in place on the patient, i.e. the device 1.1 being connected to the airway of the latter, the device 1.2 and the rings 12.1 and 12.2 being external to the patient, the channels 8.1 and the channels 8.2 are alternately fed with pressurized breathable gas(es) through the elements 9.1 to 12.1 and the elements 9.2 to 12.2, respectively, so as to alternately favour the breathing in and the breathing out of the patient.

For that purpose, a device (not shown) for the switching and the adjustment of the gas flow rates and insufflation durations is connected to the rings 9.1 and 9.2, on the one hand, and to the gas source, on the other hand.

The respiratory tubular element so constituted allows a breathing-in respiratory assistance and a breathing-out respiratory assistance, provided that a continuous flow rate ensuring the security and limiting the risk of pulmonary collapse is maintained.

The pressure in the channels 8.2 is advantageously higher than the pressure in the channels 8.1, because the effect of driving the fluid contained in the probe is not of same nature.

This dual-opposite-flow variant 22 includes a single inner tube 50 common to the two deflected-jet devices mounted head to tail. The holding fins 51 are this time arranged towards the middle of the main channel, between the outlet orifices of the auxiliary channels of the two deflected-jet devices. The inner tube extends over substantially the whole length of the main channel of this variant, its distal end 52 and its proximal end 53 coming practically at the level of the corresponding ends of the tubular elements. In a variant, two inner tubes are provided, one for each deflected-jet device, each one being present at least in the corresponding zone of the deflected jets in order to form the jet-breaker and the desired by-pass.

It is to be noted that the Figures of the present application are not at scale and that some parts of the elements shown may be more or less enlarged/elongated or reduced/shortened according to the needs. In particular, on the distal side, it is preferably made sure that the internal tube 50, as the tubular element, ends up by its distal end 52 at a level where the jets have disappeared or, at the very least, outside a zone of strong turbulence or of presence of jet(s). Indeed, this is the power of the jets and the turbulences created by these jets that are the cause of a possible nebulization or atomization. Indeed, the meeting of the deflected jets on the jet-breaking tube 50 also causes turbulences that end up being rapidly lessened towards the distal end of the tubular element.

The device of the invention may hence be intended to be introduced into or connected to an airway of a patient. It may, in other applications, constitute the tip of a mask. According to various possible applications and the type of patient (adult, child . . . ), the dimensions, in particular length and diameters, will be different.

Hence the tubular element may constitute the air inlet and outlet tip of a mask that, moreover, is of a known type, i.e. essentially comprising a shell, a sealing bead and fastening means such as straps. The tubular element used for the mask may be of the type in which the respiratory assistance acts only in the breathing-in direction (as in the case of the device of FIG. 1) but, in a variant, the mask may be equipped with a dual opposite flow device according to FIG. 6, for the breathing-in and the breathing-out assistance.

Generally, a facial respiratory mask includes a generally-truncated rigid shell, which can be applied to the face of a patient through a pad lining its peripheral opening. On the side opposite to the face, the mask is provided with a respiratory assistance device according to the present invention, including a tubular element integral with said shell or nested on a tubular protrusion of the latter.

The tubular element, for example 205 in FIGS. 7 to 10, serves as a gas inlet and outlet tip in the mask, its proximal end, opposite to the patient, being at free air, whereas its distal end, on the patient side, is connected to the mask. The respiratory gas is brought in peripheral annular chamber and to the peripheral auxiliary channels by a feeding duct connected, on one side, to a feeding tip of the device and, on the other side, to a source of respiratory gas(es), such as a pressurized gas bottle. It may be provided inside the feeding duct a plug pierced with a longitudinal passage allowing the adjustment of the gas pressure inside the device. For example, the plug may be obtained by cutting a section over the length of a profile whose longitudinal passage has a constant diameter d. It will be easily understood that, by varying the length of the plug and of the section thereof, the load loss added by the latter in the feeding duct is varied. It is hence possible, by experimentation, to adjust said load loss so that, in use, the pressure of the respiratory gas at the distal end of the tubular element corresponds to an optimum and safe oxygenation of the patient. Moreover, the tubular element includes a tip for gas sampling and/or pressure measurement.

The respiratory assistance device of the invention may, in other applications, be in the form of nasal respiratory assistance apparatus for a patient. However, given the reduced dimensions of such a nasal apparatus that must be placed at least in part within the nostrils, the efficiency of the by-pass due to a hollow inner tube will be lesser, given its smaller diameter than in the other applications.

A nasal respiratory assistance apparatus implements one device according to the invention per nostril, the two devices being arranged in parallel. This nasal apparatus is connected to a breathable gas, and possibly humidification liquid, feeding circuit. Preferably, the apparatus includes two devices of the invention within a monolithic part. Lateral tubular fittings of each of the devices are respectively connected to feeding ducts, fed in parallel with ventilation breathable gas by a feeding device, itself connected by a duct to a source of such a gas.

Optionally, if a pressure measurement is desired, a capillary tube whose distal end is provided with a lateral indentation and whose length is equal to several times the diameter of said capillary tube is inserted into one of the main channels or in the two main channels. This lateral indentation of the capillary tube is arranged in the distal part of the main channel and serves as a pressure tap at this place. The capillary tube transmits the pressure to the feeding device and to a water pressure gauge.

Optionally, if a humidification is desired, each tubular element is associated with a feeding duct in the form of a lateral duct emerging into a conical intermediate part of the corresponding main channel, between a part of greatest diameter and a distal part of smallest diameter of said main channel. The ends of said lateral ducts protrude inside the main channel and is beveled. The inclination of said bevel is opposed to that of the conical intermediate part. The lateral ducts are connected in parallel to a tank containing a liquid, for example water, potentially added with medicines or the like, and are fed with liquid from this tank, for example by gravity and/or capillarity.

It may be provided that, when after a breathing out the patient begins to breath in, the feeding device receives the corresponding pressure variation by the capillary tube and allows addressing to the patient continuous or impulsive jets, according to the needs, of breathable gas through feeding ducts. The breathable gas jets formed inside each main channel are deflected by the conical intermediate parts by carrying along the liquid droplet attached to the end bevels of the lateral ducts and are humidified. On the other hand, when after a breathing in the patient begins to breath out, the feeding apparatus is controlled to stop by the pressure transmitted by the capillary tube and the patient can freely breath out through the main channels.

It is understood that this control means acting as a function of the respiratory phases on the providing of breathable gas may be implemented in other applications than a nasal application of the device of the invention.

Foam washer may be threaded on the distal ends of the tubular ends and then serve as a flexible stop to the driving in of the monolithic part into the patient's nostrils.

The variant 205 of the device, detailed in FIGS. 7 to 10, includes an internal main channel 207, and, in median part, a conical wall 208, protruding inside said main channel 207. The conical wall 208 has for object to deflect, towards the axis of the main channel 207, jets of breathable gas(es) injected through auxiliary channels 209, fed from a feeding tip 210, through a peripheral auxiliary chamber 211.

The device 205 includes an inner tube 50 at the centre of the main channel 207, coaxial to the axis 16 of the latter. The inner tube, which is hollow, forms, on the one hand, a jet-breaker due to the fact that it passes through the zone of the deflected jets produced by the orifices of the auxiliary channels, and, on the other hand, a by-pass thanks to its lumen 54 extended between its two ends 52, 53.

In this variant, the fins 51 are extended between the inner tube 50 and a tubular body 55 that is inserted in the tubular element 4 by the proximal end of the latter. The inner tube 50, the fins 51 and the tubular body 55 can, in certain variants, form a monolithic part introduced into the proximal end of the tubular element 4. The tubular body 55 herein includes structural elements intended to form, in combination with other structural elements of the tubular element 4, the auxiliary channels 209 and the outlet orifices thereof.

Moreover, on the distal side, the device 205 includes an annular peripheral chamber 212, coaxial to said device 205. The annular peripheral chamber 212 emerges on the distal side by a distal annular passage 213. In the case where the device 205 is installed on a facial mask, the annular peripheral chamber 212 communicates with the inside of the mask through this distal annular passage 213. The annular peripheral chamber 212 is, on the proximal end, in relation with an outlet tip 214.

A fibrous or porous filter 215, for example made of cotton, synthetic foam, or other, is arranged in the annular peripheral chamber 212, to absorb the gaseous turbulences and, thereafter, the too high variations of pressure. Indeed, the outlet tip 214 may be connected, for example, to a gas analyser and/or to a pressure measurement device. Of course, the links between the outlet tip 214 and the gas analyser and/or the pressure measurement device are provided so that the gas sampling to be analysed through the link has no influence on the analysis and/or the pressure measurement, via the link.

Hence, the practitioner assisting the patient permanently knows the composition of the gas in the mask, in particular its content in carbon dioxide, and the pressure inside said mask. He can hence take suitable intervention measures as a function of said composition and pressure of the gas.

It is understood that this variant 205 can be made in a different manner while ensuring the same functions of respiratory assistance and of measurement taking. Moreover, the device may also include, in addition, means or ducts for injection of medicines and/or water, in particular for nebulization.

More generally, the device of the invention may find many other applications, for example in combination with a nasal probe, a buccal probe, a tracheal probe, etc.

The positioning of the inner tube with respect to the deflected gas jets exiting from the outlet orifices of the auxiliary channels will now be described. For that purpose, FIG. 11 details more specifically the interaction between the inner tube and the jets.

In FIG. 11 is shown only a part of a tubular element 4, more particularly a part substantially comprised between the outlet orifices 17 of the auxiliary channels 8 and the distal end 7 (to the right in the Figure but not visible) of said tubular element. The inner tube 50 is arranged centrally in the main channel 5, coaxially to the axis 16 of the latter.

In order to simplify the explanations and without this necessarily corresponds to the reality, it has been supposed that the deflected jet was undergoing specular reflections on the external surface of the internal tube and the internal surface of the tubular element. It is understood that this specular reflection of the deflected jets must not occur in reality due to the loss of energy of the gases meeting each other on the inner tube and to the turbulences that are created in the main channel but this is a simple approximation for the following of the explanations. The holding fins supporting the inner tube have not either been shown for reasons of simplification but some can be provided on the proximal and/or distal side of the tubular element, as a function of the length of the inner tube.

It is considered that this is along the jets that the pressure of the gas is the strongest, in particular for the initial deflected jet 60.1. After the first reflection on the external surface of the internet tube it becomes less and less true due to the turbulences that tend to homogenize the pressures. However, to simplify the explanations, it is considered that along the jet axes, there is a higher pressure at least in a zone close to the outlet orifices 17 of the auxiliary channels 8. After a first reflection on the inner tube 50, the jet is supposed to be sent back along the axis 60.2 towards the internal surface of the tubular element where it is reflected on a jet axis 60.3.

The inner tube 50 is hollow and is open at its two proximal 53 and distal 52 ends. For the distal end 52 of the inner tube 50, shown several possibilities of end position has been shown: 52.1, 52.2 or 52.3. In any case, it is observed that the distal end of the inner tube is at such a level that the jet axis is far away and hence in a zone where there is not a particularly high pressure with respect to the homogeneous pressure that might be met farther away on the side of the main channel distal end. This is indeed preferable to avoid, in case of distal end of the inner tube in a zone of high pressure, that the light 54 forms in fact a gas leak towards the proximal side and the environment. Moreover, there is a risk of generation of noise, in particular a whistle, if the distal end of the inner tube ends up at the level of a jet axis, in particular the first one 60.1. It is well understood that, if the distal end of the inner tube is installed, on the distal side of the tubular element, far away of the outlet orifices of the auxiliary channels, in a zone where the pressure of the gas has been homogenized, the above-mentioned potential risks disappear. That is why the exsufflation/breathing out is made as a priority through the inner tube lumen. The operation of the device of the invention with a hollow inner tube may be interpreted as a redistribution of the gas flows: the turbulences generated by the meeting between each other of the jets of the conventional devices are replaced by a redistribution of the flows: a "path" about the inner tube allows the insufflation towards the patient and another "path" in the inner tube lumen allows the exsufflation of the patient.

The proximal end 53 of the inner tube 50 has been shown substantially at the outlet orifices 17 of the auxiliary channels. In variants, it may be placed more on the side of the tubular element proximal end. This last solution may correspond to that of FIG. 1 or 7.

We will now describe a particular embodiment of the device that comes from that described in relation with FIGS. 7 to 10, i.e. a device including a tubular body 55 inserted in the proximal part of the tubular element 4.

Figure 12:
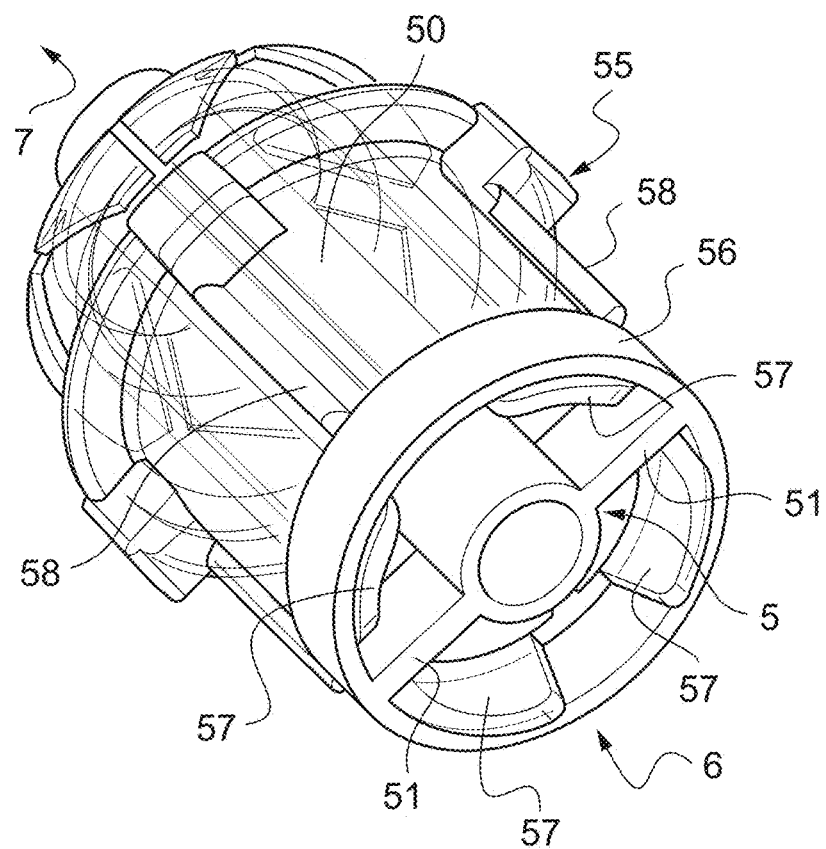
FIGS. 12 and 13 show two views of another exemplary embodiment of the invention.

In FIG. 12, the tubular body 55 is seen in a perspective view, the proximal end 6 being towards the observer. A single-piece part with an inner tube 50 is nested into the tubular body 55. The single-piece part is consisted of the hollow inner tube 50, the fins 51 and the circular ring 56. In this example, only two fins 51 are made. The tubular body 55 intended to be inserted into the proximal end of the tubular element includes structural elements intended to form some parts of the auxiliary channels 209, outlet orifices of said auxiliary channels and of the peripheral annular chamber 211.

Figure 13:
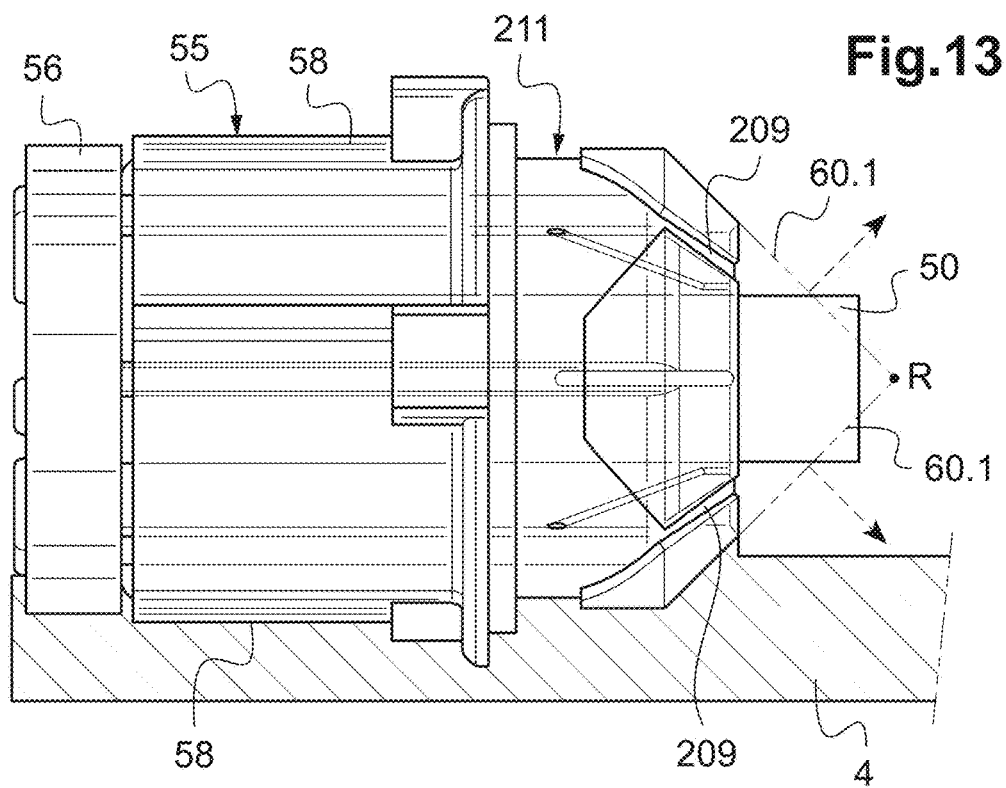

In FIG. 13 has been schematized the axes of the initial deflected jets 60.1 coming from two of the outlet orifices of the auxiliary channels. If the inner tube has been omitted, the axes would have met each other at the meeting point R as it is the case in the conventional devices of the Boussignac type. Due to the presence of the inner tube 50, the jets hit the inner tube, hence the jet-breaking effect of said inner tube.

In these FIGS. 12 and 13, the circular ring 56 comes by its external surface on the internal surface of the tubular element 4 because the single-piece part fits into the proximal end of the tubular body 55 but, in variants, the circular ring 56 will come by its external surface on the internal surface of the tubular body 55.

In a device of this type and for a CPAP of 13 mm, the internal section of passage of the inner tube is of 29 $mm^2$, which leaves about the inner tube in the main channel a section of passage 88 $mm^2$, hence a ratio of transverse surfaces of passage of about 1/3. Still in this type of device, a length of inner tube of about 43.5 mm has revealed satisfying, the distal end of the inner tube being at about 16 mm from the zone of meeting of the jets with the inner tube, the deflected jets emerging directly from the outlet orifices of the auxiliary channels. The outlet orifices of the auxiliary channels are herein un the form of semi-circular bands of 0.25 mm of thickness over a length of arc of about 1 mm.

In other variant embodiment, the device may implement a single deflected lateral jet and in this case the jet-breaking inner tube will make the jet spirally coil up about it due to the inclination of the deflected jet. The section of passage of the inner tube may be adapted to the applications provided for the device. At a pinch, the section of passage may be null, the inner tube being then only a jet-breaker with no by-pass.

Preferably, the inner tube, in particular when it is under the form of single-piece part, includes, as the parts of the device with which it is in contact, complementary positioning means and/or foolproofing means, or even plugging/locking means, so that the insertion and holding thereof is ensured in a predefined manner. For example, it may be seen in FIGS. 12 and 13 that the single-piece part nests until coming into abutment against ribs 58 of the tubular body and can no longer be pushed towards the distal side, beyond said ribs.

In FIGS. 12 and 13, the tabs 57 pass under the circular ring 56. These tabs 57 may have at their proximal ends snugs preventing the removing of the single-piece part once the latter nested. It is understood that other equivalent means can be used.

The tubular element constitutive of the embodiments of the device according to the invention may be made of any material already used in the respiratory probes, for example of polyvinyl chloride, with a potential coating made of silicon or steel, allowing the high-pressure injections.

The device with an inner tube may be removable or being fixed in place/be a part of a CPAP valve device of the Boussignac type. In the case of a removable device, it may be connected to the CPAP by a flexible tab. Preferentially, the device is designed integrated to a CPAP of the Boussignac type, hence without being an added part.

The hollow inner tube has a wall thickness the lowest possible in order not to hamper the breathing out and to generate no over-pressure. For example, it is provided a thickness of wall of the inner tube of 0.7 mm. The inner tube is designed with a suitable material that causes no resonance, for example: silicon, POM, ABS.

Preferably, the inner tube must be close to jet outlet orifices to limit optimally the noise without however clogging these orifices or hamper the exit of the jets to maintain a sufficient pressure in the device. For example, for an external diameter of 7.0 mm of the inner tube, the distance of the external surface of the inner tube to a jet outlet orifice, transverse distance in the device, is comprised between 1 mm and 5 mm.

As seen, the inner tube must have a sufficient length so as to be counter to the jets and it may even be a little longer in order to guide the gases along its wall. For example, it is provided a length of inner tube comprised between 30 mm and 55 mm, but the length of the inner tube may be reduced to 5 mm or 10 mm, for example, if it is integrated in a CPAP of the Boussignac type.

Of course, the dimensions of the device according to the invention may be very variables, essentially as a function of the application, of the way the tubular element is placed and the size of the patient, who may be an adult, a child, an infant or a premature baby.

It has been possible to show that, with the device of the invention with an inner tube, no significant modification of the performances of the CPAP valve of the Boussignac type with respect to a CPAP valve of the Boussignac type, i.e. with no inner tube, on the following parameters: generated pressure, resistance to breathing out, FiO2 rate, was noted. On the other hand, it has been possible to obtain a significant reduction of the acoustic pressure.

The device of the invention may be used in the attempts of resuscitation of persons in respiratory and/or cardiac arrest. These persons may produce liquid rejects such as expectoration, hemorrhage, hemoptysis, or even vomiting, when they are not yet intubated, etc., which may pass in the airways and be expelled through the device. Thanks to the invention, the risk of scattering them through the exit/proximal end and the risk of causing possible contaminant stains are reduced. Moreover, thanks to the inner tube, a reduction of the generated noise with respect to the conventional device with no inner tube may be obtained.

In certain conditions, it may further be provided means for filtering/holding these liquid rejections on the proximal end side of the device. These means may be a filter, for example an adapter in which the filtering mass is installed or may be so, wherein said mass can for example be a compress whose texture allows the passage of the gases. These means may be a clarifier with a clarifying container, preferably remote from the device and connected to the latter by a flexible tube. In the case where the device further includes additional functional means on the proximal side, for example braking means, then, preferably, the filtering/holding means are arranged between the device and these additional functional means. In a simpler variant, a tube is simply connected to the proximal end of the device by its first end and the other end of the tube is positioned at a place where possible stains are unimportant and/or may be collected.

Finally, in a variant implementation presented in the patent application WO2008113913 and which may be used within the framework of the present invention, the device further includes means for the spontaneous braking of the external air in the main channel via its proximal end. These means may be installed in place of the device and be a part of the latter, or being removable by connection to the proximal end of said device. Thanks to these braking means, it is possible to use the device for the resuscitation of a person in state of cardiac arrest. In this case, the device with braking means is used for the ventilation, for example through a mask or by intubation, and alternated compressions and decompressions are exerted on the thoracic cage of said person. It then occurs a braking of the entry of the external air into the device and hence towards the patient, at the beginning of each decompression. It results therefrom a drop of pulmonary pressure in the thoracic cage and hence on the heart and hence an assistance for the cardiac expansion and the blood return to the heart.

The invention claimed is:

1. A respiratory assistance device for a patient, the device comprising:
   a tubular element forming a main channel configured to be connected by a distal end thereof to an airway of the patient, said main channel configured to connect the respiratory system of said patient to the atmosphere by a proximal end thereof;
   at least one first auxiliary channel configured to allow injection through at least one distal outlet orifice of the at least one first auxiliary channel of at least one jet of breathable gas configured for ventilation of said patient, said at least one distal outlet orifice emerging into said main channel in a vicinity of the distal end of the main channel;
   a deflection system configured to allow deflection of the at least one jet of breathable gas towards an inside of said main channel and towards the distal end according to a determined inclination;
   at least one coaxial inner tube centered in the main channel, said at least one inner tube having a determined length having a distal end turned towards the distal end of the tubular element and a proximal end turned towards the proximal end of the tubular element, said determined length being such that said at least one inner tube is extended at a maximum between distal and proximal ends of said respiratory assistance device, said at least one inner tube crossing a respective axis of the at least one deflected jet in order to form a jet breaker towards a center of the main channel in a zone of meeting of said respective deflected jet axis of the at least one deflected jet and of said at least one inner tube, the at least one inner tube being hollow and open at the two ends thereof in the main channel in order to form a by-pass between the distal end and the proximal end of the main channel for the gases circulating in said main channel and for gases breathed out by the patient.

2. The device according to claim 1, wherein the at least one inner tube is held in a coaxial position inside the main channel by fins extending radially between an external surface of the inner tube and an internal surface of the tubular element, said fins being absent in the zone of the at least one deflected jet.

3. The device according to claim 2, wherein the fins and the inner tube form a single-piece part inserted into the tubular element or into a tubular body itself inserted into the tubular element.

4. The device according to claim 3, wherein the single-piece part with fins and the at least one inner tube is introduced into the tubular element through the proximal end of the tubular element, the fins being arranged only on a side of said tubular element corresponding to the proximal end and forming an obstacle to a clogging of the main channel.

5. The device according to claim 3, wherein the single-piece part with fins and the at least one inner tube includes, at a radial periphery of the fins, a circular ring having an external surface in contact with the internal surface of the tubular element or the tubular body inserted into the tubular element.

6. The device according to claim 5, wherein the tubular element includes structural elements configured to form alone or in combination with other structural elements of the circular ring or of the tubular body, in part or in totality, at least the at least one first auxiliary channel.

7. The device according to claim 5, wherein the circular ring or the tubular body includes structural elements intended to form alone or in combination with other structural elements of the tubular element, in part or in totality, the at least one first auxiliary channel and a part of the distal outlet orifice of the at least one first auxiliary channel.

8. The device according to claim 1, wherein the at least one distal outlet orifice of the at least one first auxiliary channel is one or more of punctual and annular or semi-annular band-shaped, and a diameter of the punctual orifice or a thickness of the band-shaped orifice is less than 150 micrometers.

9. The device according to claim 1, wherein the distal end of the at least one inner tube ends up in the main channel approximately at the distal end of said respiratory assistance device, and the proximal end of the at least one inner tube ends up in the main channel approximately at the proximal end of said respiratory assistance device.

10. The device according to claim 1, wherein the device is of a dual opposite flow device, enabling the patient to breathe in and breathe out, and
the device further comprises at least one additional auxiliary channel, independent of the at least one first auxiliary channel of the at least one jet of the main channel distal end, and connected to a source of pressurized gas, said at least one additional auxiliary channel emerging into the main channel in a vicinity of the proximal end of the main channel, at least one proximal end of said at least one additional auxiliary channel emerging through at least one respective proximal outlet orifice into the main channel being parallel to the main channel, a deflection system being provided opposite each of the at least one proximal outlet orifice of the corresponding at least one additional auxiliary channel, the deflection system being configured to deflect the gas jet passing through the at least one additional auxiliary channel towards the inside of said main channel, in order to form at least one jet at the proximal end of the main channel, and
two zones of deflected jets corresponding respectively to the at least one jet of the main channel distal end and to the at least one jet of the main channel proximal end each include the at least one inner tube, wherein said at least one inner tube is configured to be extended to be unique and common to the two zones or each of the zones includes its own inner tube.

11. The device according to claim 1, further comprising a brake configured to brake entry of breathing-in gases from the atmosphere to the patient, the brake being configured to brake passage of the gases only during a breathing-in phase that is a beginning of the breathing in, in order to cause an intrathoracic depression favorable to a venous return towards the heart.

12. The device according to claim 2, further comprising:
a visual indicator of direction and strength of a gaseous flow passing through the device, the visual indicator being internally disposed within the device, said indicator being a flexible strip made of plastic material, fastened at one of two ends thereof to one of the holding fins of the at least one inner tube.

13. A nasal respiratory assistance apparatus for a patient, the apparatus comprising:
for each nostril, the device according to claim 1,
the two devices being fed with breathable gases in parallel.

14. A respiratory assistance mask comprising:
the device according to claim 1.

* * * * *